(12) United States Patent
Chen et al.

(10) Patent No.: US 10,428,967 B2
(45) Date of Patent: Oct. 1, 2019

(54) VALVES HAVING PROTECTIVE COATINGS

(75) Inventors: Carl G. Chen, Hawthorn (AU); Robert A. Jencks, Mendon, MA (US); Wen Lu, Singapore (SG); Mark W. Moeller, Kingston, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 490 days.

(21) Appl. No.: 14/113,388

(22) PCT Filed: Apr. 20, 2012

(86) PCT No.: PCT/US2012/034343
§ 371 (c)(1),
(2), (4) Date: Jan. 8, 2014

(87) PCT Pub. No.: WO2012/148794
PCT Pub. Date: Nov. 1, 2012

(65) Prior Publication Data
US 2014/0137967 A1    May 22, 2014

Related U.S. Application Data

(60) Provisional application No. 61/478,778, filed on Apr. 25, 2011.

(51) Int. Cl.
*F16K 11/065* (2006.01)
*F16K 25/00* (2006.01)
(Continued)

(52) U.S. Cl.
CPC ........ *F16K 25/005* (2013.01); *C23C 14/0605* (2013.01); *F16K 11/0655* (2013.01);
(Continued)

(58) Field of Classification Search
CPC .................. F16K 11/065; G01N 30/20; Y10T 137/86638; Y10T 137/86863; C23C 14/0605; C23C 16/26
(Continued)

(56) References Cited

U.S. PATENT DOCUMENTS 5,482,602 A * 1/1996 Cooper ............... C23C 14/0605
204/192.11
5,747,120 A * 5/1998 McLean, II ......... C23C 14/0605
427/122
(Continued)

FOREIGN PATENT DOCUMENTS

JP    2006-073069 A    3/2006
JP    2008-191384 A    8/2008
(Continued)

OTHER PUBLICATIONS

Extended European Search Report for Application No. 12776051.0, dated Sep. 29, 2014 (7 pages).
(Continued)

*Primary Examiner* — Michael R Reid
*Assistant Examiner* — Christopher D Ballman
(74) *Attorney, Agent, or Firm* — Schmeiser, Olsen & Watts LLP (57) ABSTRACT

A shear valve for use in a high performance liquid chromatography system. The shear valve includes a first valve member having a plurality of first fluid-conveying features, and a second valve member having one or more second fluid-conveying features. The second valve member is movable, relative to the first valve member, between a plurality of discrete positions such that, in each of the discrete positions, at least one of the one or more second fluid-conveying features overlaps with multiple ones of the first fluid conveying features to provide for fluid communication
(Continued)

therebetween. At least one of the first and second valve members is at least partially coated with a protective coating that includes an adhesion interlayer and a diamond-like carbon (DLC) layer. The DLC layer is deposited on the adhesion interlayer via filtered cathodic vacuum arc (FCVA) deposition.

9 Claims, 5 Drawing Sheets

(51) Int. Cl.
*G01N 30/20* (2006.01)
*C23C 14/06* (2006.01)
*F16K 11/074* (2006.01)
*G01N 30/16* (2006.01)

(52) U.S. Cl.
CPC .......... *F16K 11/0743* (2013.01); *G01N 30/20* (2013.01); *G01N 30/16* (2013.01); *G01N 2030/201* (2013.01); *G01N 2030/202* (2013.01); *G01N 2030/207* (2013.01); *Y10T 137/86638* (2015.04); *Y10T 137/86863* (2015.04)

(58) Field of Classification Search
USPC .................. 137/625.46, 625.21; 204/192.38; 251/368
See application file for complete search history.

(56) References Cited

U.S. PATENT DOCUMENTS

| | | | | |
|---|---|---|---|---|
| 6,664,784 | B1* | 12/2003 | Hayashi | ................. B82Y 10/00 324/252 |
| 7,060,167 | B2 | 6/2006 | Murakami et al. | |
| 8,881,582 | B2* | 11/2014 | Dourdeville et al. | ....... 73/61.57 |
| 2002/0007796 | A1 | 1/2002 | Gorokhovsky | |
| 2003/0030023 | A1* | 2/2003 | Wang | ........................ F15C 5/00 251/331 |
| 2004/0118455 | A1 | 6/2004 | Welty et al. | |
| 2006/0044679 | A1 | 3/2006 | Ookawa et al. | |
| 2007/0023890 | A1* | 2/2007 | Haluzak | .............. B81C 1/00285 257/704 |
| 2009/0145205 | A1* | 6/2009 | Hochgraeber et al. | ...... 73/61.55 |
| 2009/0162572 | A1 | 6/2009 | Veerasamy et al. | |
| 2010/0032643 | A1* | 2/2010 | Xu | ....................... H01L 45/1641 257/4 |
| 2010/0096411 | A1 | 4/2010 | Deans | |
| 2010/0276617 | A1 | 11/2010 | Yasunaga | |
| 2010/0281959 | A1 | 11/2010 | Berndt | |
| 2010/0314247 | A1 | 12/2010 | Takashima et al. | |
| 2011/0140367 | A1* | 6/2011 | Shi | ........................ C23C 14/025 277/442 |
| 2011/0293909 | A1* | 12/2011 | Ni | ........................ C23C 14/024 428/213 |
| 2012/0132013 | A1* | 5/2012 | Glatz et al. | ................. 73/863.02 |
| 2013/0284959 | A1 | 10/2013 | Hochgraeber et al. | |

FOREIGN PATENT DOCUMENTS

| | | |
|---|---|---|
| JP | 2008-297477 A | 12/2008 |
| JP | 2014-507646 A | 3/2014 |
| WO | 2010096411 | 8/2010 |
| WO | 2011014414 | 2/2011 |

OTHER PUBLICATIONS

Japanese Search Report for Application No. 2014-508440, dated Jan. 28, 2016 (96 pages).

Japanese Office Action for Application No. 2014-508440, dated Mar. 22, 2016 (14 pages).

Kelly et al; Characterization of a Quarter Torus Filter for Vacuum Arc Ion Flux Transmission, Brazilian Journal of Physics, vol. 34, No. 4B, Dec. 2004, p. 1513-1517.

PCT International Search Report for PCT/US2012/034343, dated Jun. 28, 2012, 2 pages.

PCT International Written Opinion Report for PCT/US2012/034343, dated Jun. 28, 2012, 5 pages.

* cited by examiner

VALVES HAVING PROTECTIVE COATINGS

CROSS REFERENCE TO RELATED APPLICATIONS

This application is the National Stage of International Application No. PCT/US2012/034343, filed on Apr. 20, 2012, which claims priority to and benefit of U.S. Provisional Patent Application Ser. No. 61/478,778, filed Apr. 25, 2011. The entire contents and teachings of these applications of are hereby expressly incorporated herein by reference in their entirety.

TECHNICAL FIELD

This invention generally relates to valves, and, more particularly, to valves having protective coatings.

BACKGROUND

Many analytic systems incorporate valves for controlling fluid flow. An example is the use of shear valves in some chromatography systems. These valves often must retain fluid integrity, that is, such valves should not leak fluids. As a valve is cycled, however, between positions, the loads placed on the moving parts cause wear.

Some valves are subjected to high pressures. For example, sample injector valves in high performance liquid chromatography (HPLC) apparatus, are exposed to pressures approximately 1,000 to 5,000 pounds per square inch (psi), as produced by common solvent pumps. Higher pressure chromatography apparatus, such as ultra high performance liquid chromatography (UHPLC) apparatus, have solvent pumps that operate at pressures up to 15,000 psi or greater.

As the pressure of a system increases, wear and distortion of a valves components, such as a rotor and a stator, tends to increase, and the valve's expected lifetime may be reduced.

SUMMARY

The invention arises, in part, from the realization that a valve having sliding components can advantageously be provided with a protective coating that is deposited via a process called filtered cathodic vacuum arc (FCVA) deposition to extend the operating life of the valve operating under high pressure working conditions. Thus, for example, the invention is particularly well suited to provide improved rotary shear injection valves for delivery of samples in an HPLC or high-pressure apparatus.

In one aspect, the invention provides a shear valve for use in a high performance liquid chromatography system. The shear valve includes a first valve member having a plurality of first fluid-conveying features, and a second valve member having one or more second fluid-conveying features. The second valve member is movable, relative to the first valve member, between a plurality of discrete positions such that, in each of the discrete positions, at least one of the one or more second fluid-conveying features overlaps with multiple ones of the first fluid conveying features to provide for fluid communication therebetween. At least one of the first and second valve members is at least partially coated with a protective coating that includes an adhesion interlayer and a diamond-like carbon (DLC) layer. The DLC layer is deposited on the adhesion interlayer via filtered cathodic vacuum arc (FCVA) deposition.

In another aspect, the invention provides a shear valve for use in a high performance liquid chromatography system. The shear valve includes a first valve member and a second valve member. At least one of the first and second valve members is movable relative to the other, and one of the first and second valve members includes a plurality of ports, and the other includes at least one fluid conduit for providing fluid communication between respective ones of the ports depending on a relative position of the first and second valve member with respect to each other. The first valve member is at least partially coated with a protective coating that includes an adhesion interlayer and a diamond-like carbon (DLC) layer. The DLC layer is deposited on the adhesion interlayer via filtered cathodic vacuum arc (FCVA) deposition.

According to another aspect, the invention features a method that includes depositing an adhesion interlayer on a shear valve member via filtered cathodic vacuum arc (FCVA) deposition; and depositing a diamond-like carbon layer on the adhesion layer via FCVA deposition.

Implementations may include one or more of the following features.

In some implementations, the first valve member is formed of 316 stainless steel.

In certain implementations, the adhesion interlayer is deposited on the at least one of the first and second valve members via FCVA deposition.

In some cases, the adhesion interlayer includes an interlayer material selected from aluminum, chromium, molybdenum, silicon, tantalum, and titanium.

In certain cases, the adhesion interlayer has a thickness of about 100 nanometers to about 500 nanometers.

In some examples, the DLC layer has a hardness of about 30 GPa to about 60 GPa.

In certain examples, the DLC layer has a thickness of about 0.5 microns to about 2.5 microns.

In some implementations, the protective coating has a roughness Ra of 5 nanometers or less.

In certain implementations, the protective coating is deposited on a surface of the first valve member or the second valve member having a roughness Ra of less than 25 nanometers.

In some cases, the second valve member is rotatable, relative to the first valve member, to move between the plurality of discrete positions.

In certain cases, the shear valve is a rotary shear valve in which the first valve member includes a stator and the second valve member includes a rotor.

In some examples, the thickness of the protective coating has a variation of less than 10%.

In some implementations, the shear valve member is a stator, and the adhesion interlayer is deposited on a stator interface of the stator.

In certain implementations, the adhesion interlayer is deposited at a process temperature below 80 degrees Celsius.

In some cases, the diamond-like carbon layer is deposited at a process temperature below 80 degrees Celsius.

In certain cases, a surface region of the shear valve member is polished to a roughness Ra of less than 25 nanometers, wherein the adhesion interlayer and the DLC layer are deposited on the surface region.

In some examples, a workpiece bias voltage is adjusted during deposition of the DLC layer to provide the DLC layer with a hardness of about 30 GPa to about 60 GPa.

Implementations can provide one or more of the following advantages.

The application of diamond-like carbon (DLC) coatings to valve surfaces via a vacuum deposition technique called filtered cathodic vacuum arc (FCVA) deposition can help to extend the operating life of a valve operating under high pressure working conditions.

In some cases, an adhesion promoting material is used to help bond a DLC coating to a valve surface. The use of an adhesion promoting material that forms strong bonds with the surface being coated and has high affinity to carbon can help to provide improved adhesion of the DLC coating to the surface being coated, which can be particularly beneficial for high pressure applications. Such improved adhesion can help to inhibit defects that lead to coating fracture and delamination.

In some implementations, the use of filtered cathodic vacuum arc (FCVA) deposition for providing a protective coating can help to inhibit macroparticle contamination of the coated surface. A reduction in macroparticle contamination can help to inhibit premature wear at the coated surface.

Due to the nature of FCVA deposition, film growth at the surface being coated is intrinsically amorphous (non-crystalline), and, as a result, undesirable surface morphology due to partially crystalline film growth, which may require post-polishing and a corresponding increased production cost, can be avoided.

Other aspects, features, and advantages are in the description, drawings, and claims.

BRIEF DESCRIPTION OF THE DRAWINGS

Like reference numbers indicate like elements.

DETAILED DESCRIPTION

A valve can be provided with a protective coating, which can be applied via filtered cathodic vacuum arc (FCVA) deposition, to help to reduce wear occurring between valve members and thereby extending the operating life of the valve.

Figure 1:
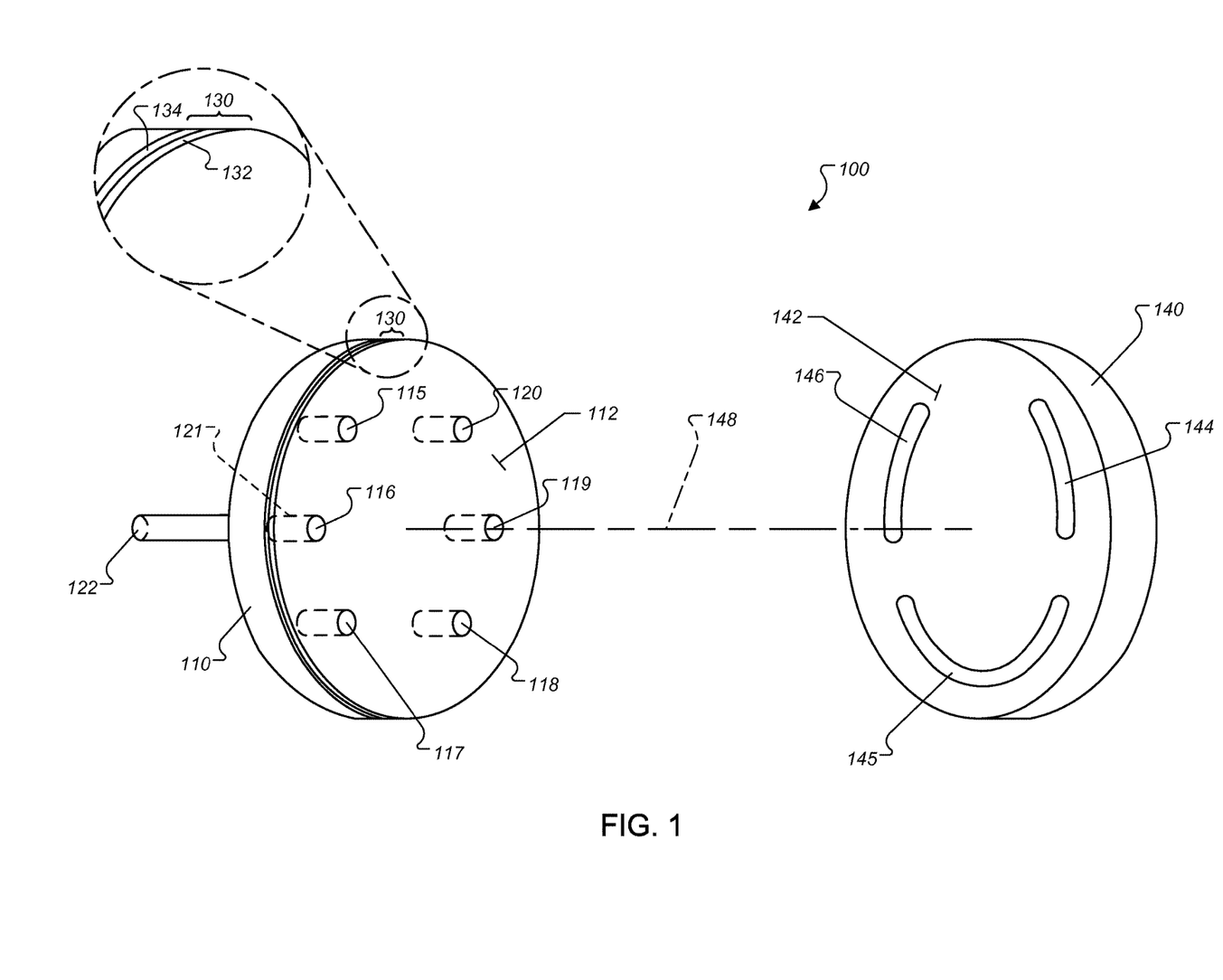
FIG. 1 is an exploded perspective view of a rotary shear valve that includes a stator having a protective coating.

Referring to FIG. 1, a six-port rotary shear valve 100 includes a stator 110 and a rotor 140. The stator 110 has a stator interface 112 and a plurality of ports 115-120. Each of ports 115-120 includes a passage (shown at 121 in the case of the port 116) which connects the port on the stator interface 112 to the rear of the stator 110. Fluid connections to the ports 115-120 can then be made via the passages (e.g., the pipe 122 in the case of passage 121). The connection can include a socket formed in the stator 110 for receiving a ferrule fitted to the pipe and a suitable securing nut, as in the case of a conventional pipe union.

The ports 115-120 can be approximately 0.006 inches diameter and can be arranged in a circular array of diameter 0.1 inches. The external diameter of the stator 110 can be about 0.15 inches. The stator 110 can manufactured from stainless steel (e.g., 316 stainless steel), or other corrosion resistant alloy. The stator interface 112 can be provided with a protective coating 130, which can help to reduce wear, and, consequently, extend the operating life of the valve 100. The protective coating 130 includes a diamond-like carbon layer 132 and an adhesion interlayer 134 disposed between and in intimate contact with the stator interface 112 and the DLC layer 132. The DLC layer 132 and the adhesion interlayer 134 can be applied via a technique called filtered cathodic vacuum arc (FCVA) deposition.

The rotor 140 has a rotor interface 142, which includes three fluid conduits 144, 145, 146 in the form of arcuate grooves, which link pairs of adjacent ports 115-120. When assembled, the rotor interface 142 is urged into contact with the stator interface 112, e.g., by pressure exerted on the rotor 140 by a spring, to help ensure a fluid-tight seal therebetween. The rotor 140 is capable of rotation about an axis 148 and has two discrete positions relative to the stator 110. In a first position, groove 144 overlaps and connects ports 115 and 116, groove 145 overlaps and connects ports 117 and 118, and groove 146 overlaps and connects ports 119 and 120. In the second position, groove 144 overlaps and connects ports 116 and 117, groove 145 overlaps and connects ports 118 and 119, and groove 146 overlaps and connects ports 120 and 115.

The diameter of the rotor 140 can be about 0.200 inches. The fluid conduits 144, 145, 146 can consist of 0.008 inch wide by 0.008 inch deep arcuate grooves extending for 60°, spaced apart along a circular path of the same diameter of the array of ports (0.1 inches). The rotor 140 can be manufactured from polyether-ether-ketone, such as PEEK™ polymer (available from Victrex PLC, Lancashire, United Kingdom), filled with between 20 and 50% carbon fiber. Alternatively or additionally, the rotor 140 can be manufactured from polyimide (available as DuPont™ VESPEL® polyimide from E.I. du Pont de Nemours and Company), or polyphenylene sulfide (PPS).

Figure 2A:
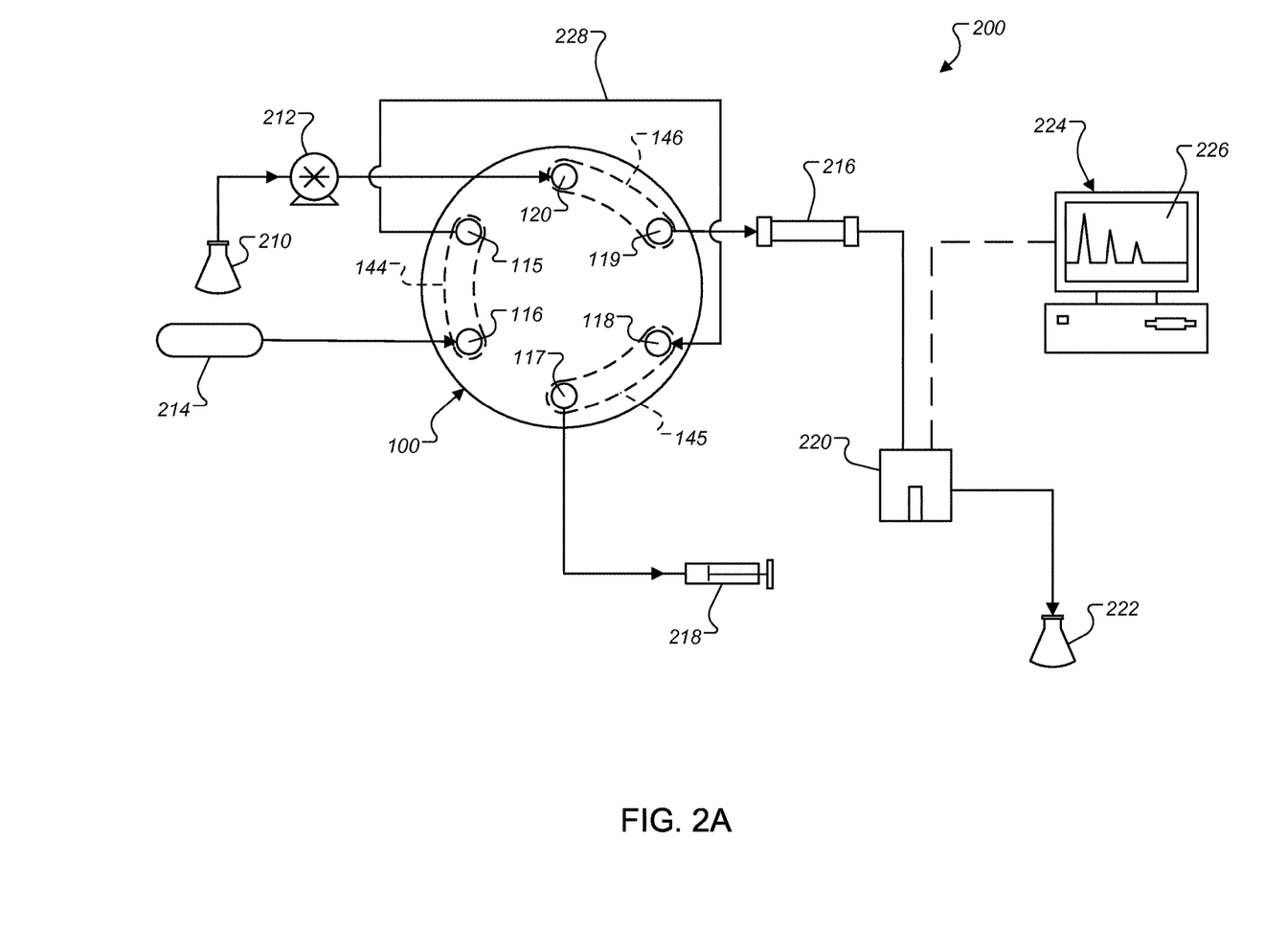
FIGS. 2A and 2B are schematic views of a high performance liquid chromatography system including the rotary shear valve of FIG. 1.
Figure 2B:
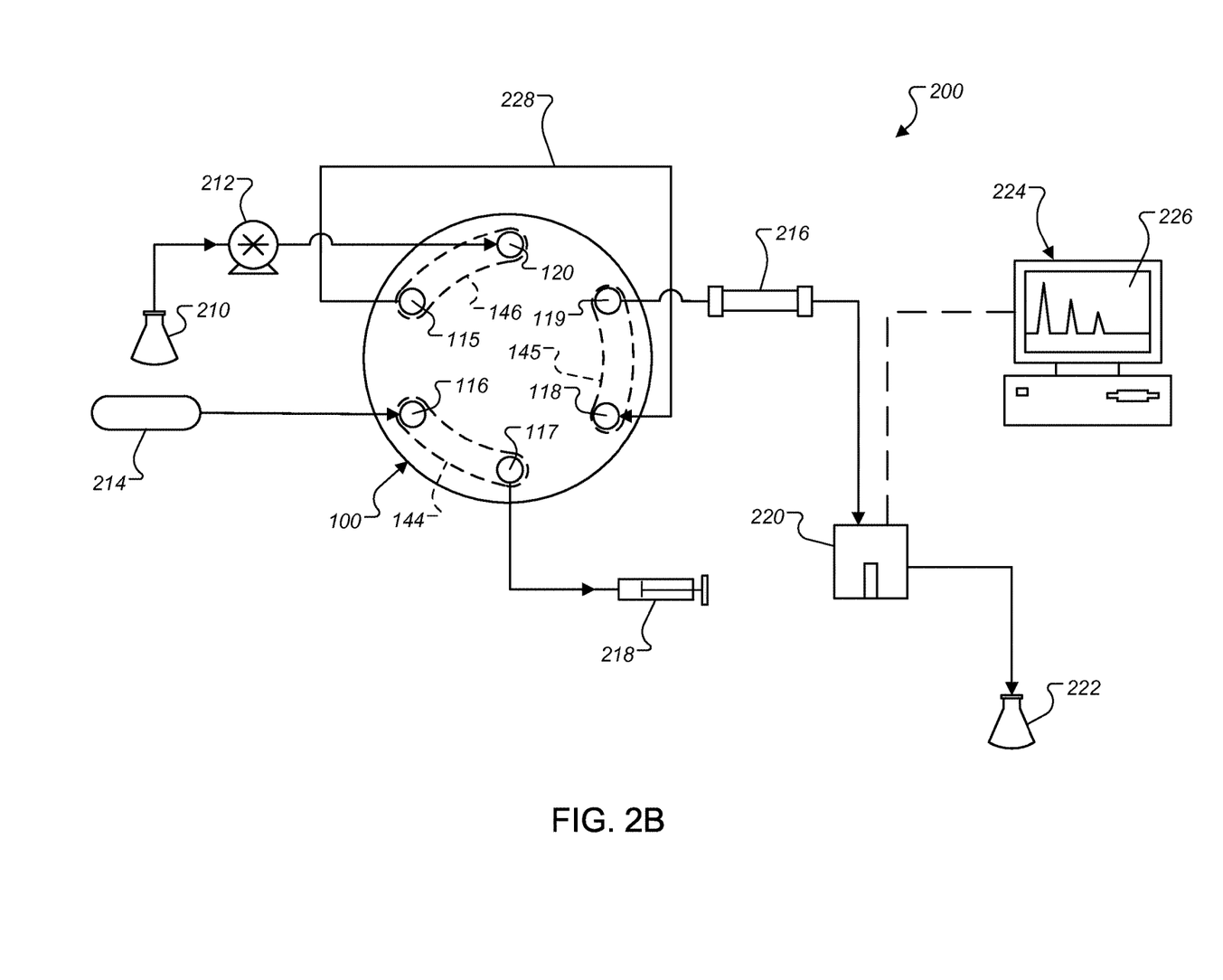

A valve with this configuration can be used for injecting samples into the flow of a fluid for subsequent chromatographic analysis, both for gas chromatography and for liquid chromatography. For example, FIGS. 2A and 2B illustrate a high performance liquid chromatography (HPLC) system 200 that incorporates the six-port rotary shear valve 100 of FIG. 1. Referring to FIGS. 2A and 2B, a carrier fluid reservoir 210 holds a carrier fluid. A carrier fluid pump 212 is used to generate and meter a specified flow rate of the carrier fluid, typically milliliters per minute. The carrier fluid pump 212 delivers the carrier fluid to the valve 100. A sample, from a sample source 214 (e.g., a sample vial), is introduced into the valve 100 where it can combine with the flow of carrier fluid, which then carries the sample into a chromatography column 216. In this regard, the sample may be aspirated from the sample source 214 through the action of an aspirator 218 (e.g., a syringe assembly). A detector 220 is employed to detect separated compound bands as they elute from the chromatography column 216. The carrier fluid exits the detector 220 and can be sent to waste 222, or collected, as desired. The detector 220 is wired to a computer data station 224, which records an electrical signal that is used to generate a chromatogram on its display 226.

In use, when the valve 100 is in a first position (FIG. 2A), port 115 is in fluid communication with port 116, port 117 is in fluid communication with port 118, and port 119 is in fluid communication with port 120. In this first position, the sample flows into the valve 100 via port 116 and then into a sample loop 228 (e.g., a hollow tube) via port 115, and carrier fluid is delivered into the valve 100 via port 120 and then toward the chromatography column 216 and the detector 220 via port 119.

When the valve's rotor is rotated into a second position (FIG. 2B), port 115 is placed in fluid communication with port 120, port 116 is placed in fluid communication with port 117, and port 118 is placed in fluid communication with port 119. In this second position, the carrier fluid is conveyed through the sample loop 228, where it merges with the sample, and then carries the sample downstream to the chromatography column 216 and the detector 220.

For some liquid chromatography applications, the valve 100 may have to operate at under pressure conditions of above 10,000 pounds per square inch (psi). The mechanical wear and tear on the valve stator and rotor under these extreme pressure conditions can reduce the operating life of the valve. However, the application of the protective coating 130 to the stator interface 112, via FCVA deposition, can help to extend the valve life under these high pressure working conditions.

Figure 3:
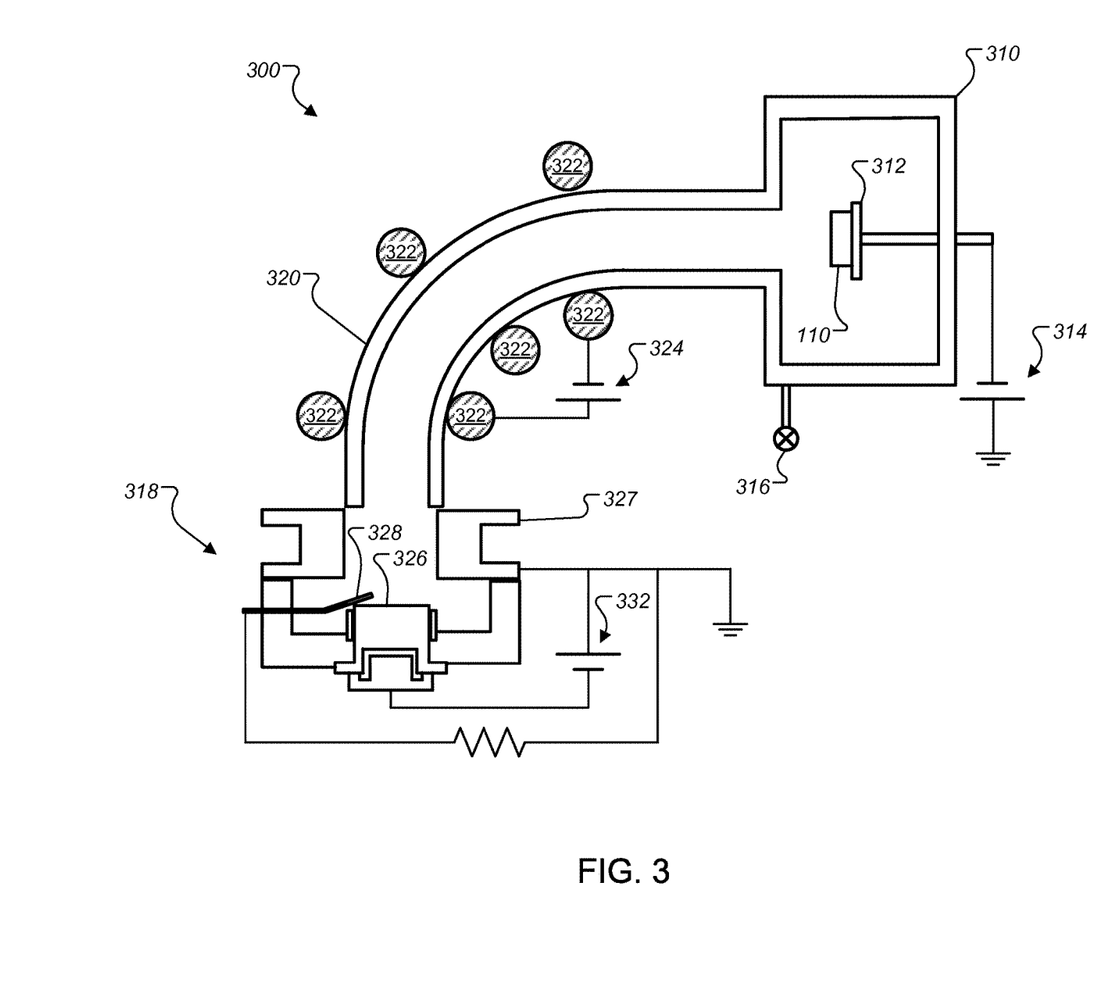
FIG. 3 is a schematic view of a filtered cathodic vacuum arc apparatus.

FIG. 3 illustrates an exemplary FCVA apparatus 300 that can be used to apply a protective coating to one or more surfaces of the valve, such as the stator interface 112 of the stator 110.

The FCVA apparatus 300 includes a deposition chamber 310, in which a holder 312 is arranged for supporting a workpiece. In this example the stator 110 is the workpiece. The holder 312 is connected to a workpiece bias source 314, which applies a bias voltage to the workpiece held by the holder during a deposition process.

The disposition chamber is connected to a vacuum source 316, which can provide a vacuum state in the deposition chamber 310. A vapor source 318 is in communication with the deposition chamber 310 via a curved (e.g., quarter-turn) duct 320. A first end of the duct 320 is connected to the deposition chamber 310 and the vapor source 318 is arranged adjacent a second, opposite end of the duct 320.

A coil 322 is disposed around the duct 320 and is connected to a filter bias source 324 which energizes the coil 322 to form a magnetic field. The duct 320 and the coil 322 form a magnetic filter, which operates when energized by the filter bias source 324.

The vapor source 318 includes a cathode 326, which consists of a target material corresponding to the film to be deposited, and a trigger electrode 328. The vapor source 318 also includes an arc power source 332 for applying an arc discharge voltage across the cathode 326 and the anode 330, and for applying a trigger voltage across the cathode 326 and the trigger electrode 328 to induce an arc discharge between the cathode 326 and the anode 330.

In FCVA deposition, plasma is generated in the arc discharge between the target material, acting as the cathode, and the anode which is held at ground. The plasma contains ions of the target material. Magnetic fields steer the ions toward a negatively charged workpiece and filter out macroparticle contamination as well as neutral species.

Magnetic filtering and workpiece biasing help to ensure that only ions of uniform energy strike and coat the workpiece. Unlike physical vapor deposition (PVD) processes, such as direct arc plasma deposition and magnetron sputtering, FCVA coatings are substantially devoid of any macroparticle contaminant. Since no hydrocarbon reaction is required, spontaneous nucleation of solid particles as in (PACVD) is also absent. As a result, valve parts, such as the stator, can be coated with a layer of highly conformal, dense and substantially defect free amorphous DLC film.

Figure 4:
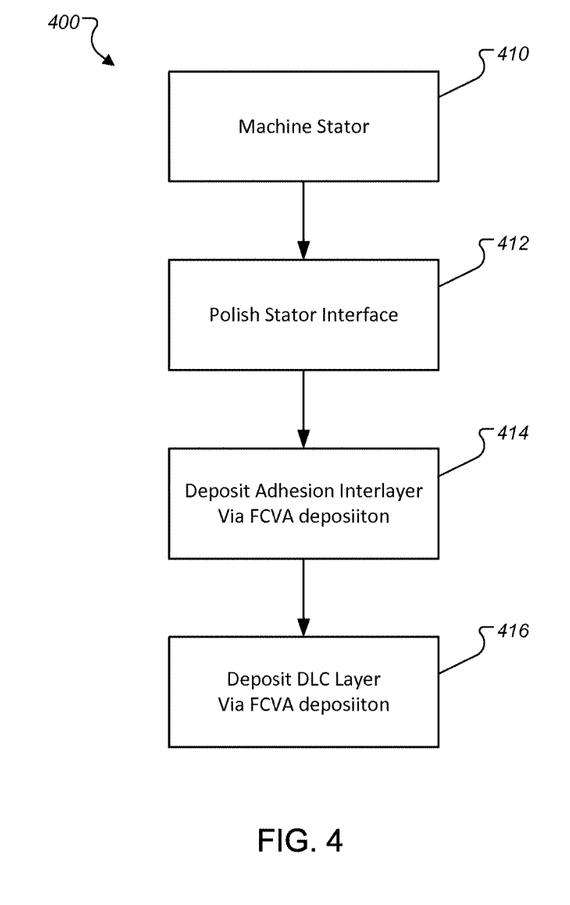
FIG. 4 is an exemplary process for fabricating a valve member having a protective coating.

FIG. 4 illustrates an exemplary process for fabricating the stator 110. First, the stator 110 is machined (410), e.g., to form the ports 215-220 (FIG. 1), and the stator interface 112 is polished to the desired surface finish (412).

Once the stator 110 is machined and polished, the adhesion interlayer 134 (FIG. 1) is deposited on the stator 110 using FCVA deposition (414). Since iron carbide has a net positive enthalpy of formation which indicates relatively poor binding of carbon to iron atoms, the adhesion interlayer 134 can be used to secure the adhesion of the DLC layer 132 to the (stainless steel) stator 110. The FCVA apparatus 300 can be used to apply the adhesion interlayer 134. In this regard, the stator 110 is mounted in the holder 312 and an interlayer material is employed as the target/cathode 326 for forming the adhesion interlayer 134.

The choice of a suitable interlayer material for promoting adhesion to steel lies in the material's affinity to carbon to form stable carbide. From an energy-of-carbide-formation point of view, the following transition metals and semiconductor elements are suitable interlayer material candidates: aluminum, chromium, molybdenum, silicon, tantalum, and titanium. For example, chromium and titanium can be conveniently deposited by FCVA and both targets are commercially available. In some implementations, titanium is used as the interlayer material as its enthalpy of carbide formation is more than twice that of chromium, resulting in a stronger bond to the DLC layer 132, and the thermal expansion of titanium is also better matched to that of 316 stainless steel.

The DLC layer 132 can then be deposited over the adhesion interlayer 134 using FCVA deposition (418). In this regard, the FCVA apparatus 300 described above, with reference to FIG. 3, can also be used to apply the DLC layer 132, e.g., by replacing the interlayer material target used for providing the adhesion interlayer 134 with a pure graphite target. In some cases, the FCVA apparatus has an external vapor source, and yields a process temperature below 80 degrees Celsius. The essentially room temperature can help to prevent high temperature induced thermal damage to the coated workpiece and can help to prevent sp3 to sp2 carbon bond transition which can reduce the coating hardness. For LC applications of above 10,000 psi, it can be desirable to have a DLC layer 132 of high hardness in order to reduce the material wear rate. In some implementations, the DLC layer 132 has a specified hardness of 30 GPa to 60 GPa, which is obtainable by adjusting the workpiece bias voltage during the deposition process. Due to the nature of FCVA, film growth at the workpiece is intrinsically amorphous (non-crystalline).

The thickness of the coating, including the adhesion interlayer 134 and the DLC layer 132, is preferably controlled to a variation of less than 10%. If the coating is too thin, there may not be the necessary mechanical compliance required to form a high pressure seal. On the other hand, if the coating is too thick, its internal stress increases, which may lead to early stress fractures and delamination. Thick FCVA coatings also take longer to deposit and may necessitate increased production cost.

The thickness of the adhesion interlayer 134 is nominally proportional to the thickness of the DLC layer 132, and both are dependent on the nature of the films to be deposited, such as the choice of the interlayer material and the desired DLC properties, as well as the related functional specifications, such as LC system pressure, part geometry and required coating compliance.

In one example, the stator 110 is formed of 316 stainless steel and is provided with a titanium adhesion interlayer with a thickness of about 100 nanometers to about 500 nanometers, and a DLC layer with a thickness of about 0.5 micron to about 2.5 microns. In the region of the stator interface 112, the 316 stainless steel stator 110 is polished to a finish Ra of less than 25 nanometers. The FCVA deposited protective coating at the stator interface 112 has a roughness of no more than 5 nanometers (e.g., 2 to 4 nanometers). In this example, the protective coating is conformal over the entire seal face, with the Ra of the coated surface equal to or less than the roughness Ra of the uncoated surface. No post-polishing is required, which can save manufacturing cost. The coefficient of friction of the protective coating can less than 0.2 (e.g., less than 0.1) depending on the desired coating hardness and sp3 carbon fraction.

Although a few implementations have been described in detail above, other modifications are possible. For example, while an example been described in which a FCVA deposited protective coating is applied to a stator interface, the workpiece to be coated can be any conductive liquid chromatography (LC) valve parts, including, but not limited to, stators and/or rotors made in part of metal such as stainless steel, aluminum, titanium, and their alloys.

The FCVA deposited protective coatings described herein can be applied to rotary shear injector valves of any port geometry, to other valves used in LC such as vent valves, solvent selector valves, and, more generally, to other valves and mechanical devices that operate under similar mechanical principles of having a shear force dominated sliding contact interface.

In some examples, both the stator and the rotor interfaces can be independently coated with a protective coating to enable further improved chemical inertness, wear rate, and/or friction coefficient.

Because the hardness of the protective coating is tunable over a large range, one of the valve members (e.g., the stator) can be provided with a protective coating of high hardness and the other one of the valve members (e.g., the rotor) can be provided with a protective coating of comparatively low hardness. In one example, the stator is coated with a DLC layer having a hardness of 30 GPa to 60 GPa and the rotor is coated with a DLC layer having a hardness of 20 GPa to 30 GPa.

Accordingly, other implementations are within the scope of the following claims.

What is claimed is:

1. A method comprising:
   depositing an adhesion interlayer on a shear valve member via filtered cathodic vacuum arc (FCVA) deposition, the adhesion layer including an interlayer material consisting of titanium; and
   depositing a diamond-like carbon (DLC) layer on the adhesion layer via FCVA deposition;
   wherein the diamond-like carbon layer on the adhesion layer has a thickness of about 0.5 microns to about 2.5 microns and a roughness Ra of 5 nanometers or less.

2. The method of claim 1, wherein the shear valve member is a stator, and wherein depositing the adhesion interlayer comprises depositing the adhesion interlayer on a stator interface of the stator.

3. The method of claim 1, wherein the adhesion interlayer is deposited at a process temperature below 80 degrees Celsius.

4. The method of claim 1, wherein the diamond-like carbon layer is deposited at a process temperature below 80 degrees Celsius.

5. The method of claim 1, further comprising:
   polishing a surface region of the shear valve member to a roughness of less than 25 nanometers,
   wherein the adhesion interlayer and the DLC layer are deposited on the surface region.

6. The method of claim 1, further comprising adjusting a workpiece bias voltage during deposition of the DLC layer to provide the DLC layer with a hardness of about 30 GPa to about 60 GPa.

7. The method of claim 1, wherein the deposited adhesion interlayer has a thickness of about 100 nanometers to about 500 nanometers.

8. The method of claim 1, wherein each of the adhesion interlayer and the DLC layer has a thickness greater than 5 nanometers.

9. The method of claim 1, wherein the roughness Ra of the DLC layer is achieved without post-polishing.

* * * * *